United States Patent
Gaillard et al.

(10) Patent No.: US 8,601,713 B2
(45) Date of Patent: Dec. 10, 2013

(54) SILENCER FOR DRYING APPLIANCE AND QUIET HAIRDRYER

(75) Inventors: Christophe Gaillard, Romorantin-Lanthenay (FR); Michel Guillosson, Olivet (FR); Roland Quessard, Romorantin-Lanthenay (FR)

(73) Assignee: Velecta Paramount S.A., Romorantin-Lanthenay (FR)

( * ) Notice: Subject to any disclaimer, the term of this patent is extended or adjusted under 35 U.S.C. 154(b) by 569 days.

(21) Appl. No.: 12/864,140

(22) PCT Filed: Jan. 26, 2009

(86) PCT No.: PCT/FR2009/000081
§ 371 (c)(1),
(2), (4) Date: Oct. 13, 2010

(87) PCT Pub. No.: WO2009/112690
PCT Pub. Date: Sep. 17, 2009

(65) Prior Publication Data
US 2011/0016737 A1 Jan. 27, 2011

(30) Foreign Application Priority Data
Jan. 25, 2008 (FR) ...................................... 08 00396

(51) Int. Cl.
*A45D 20/12* (2006.01)
(52) U.S. Cl.
USPC ............... 34/97; 181/269; 415/119; 132/221; 60/796
(58) Field of Classification Search
USPC ............... 34/60, 80, 86, 95, 96, 97, 100, 105; 181/269; 415/119, 121.2, 208.1; 132/200, 221; 60/785, 796; 417/312
See application file for complete search history.

(56) References Cited

U.S. PATENT DOCUMENTS 3,286,786 A * 11/1966 Wirt ............................... 181/213
3,286,787 A * 11/1966 Wirt ............................... 181/213
(Continued)

FOREIGN PATENT DOCUMENTS

DE 31 41 245 A1 4/1983
DE 88 05 910 U1 6/1988
(Continued)

OTHER PUBLICATIONS

Notice of Allowance mailed May 3, 2012, co-pending U.S. Appl. No. 12/048,810.
(Continued)

*Primary Examiner* — Steve M Gravini
(74) *Attorney, Agent, or Firm* — Miles & Stockbridge P.C.

(57) ABSTRACT

The present invention relates to a silent hair dryer (3) comprising at least one casing (30) comprising an inlet end (33) and an outlet end (31) and enclosing at least one turbine (T) sucking in air via at least one admission orifice (330) upstream of the turbine (T) and expelling it downstream via at least one outlet orifice (310), and generating determined sound frequencies, characterized in that it comprises a silencer comprising at least one chamber (10) upstream of the admission orifice (330) and comprising an inlet orifice (110) for aspiration of air upstream of the chamber (10), the diameter of the chamber (10) being greater than the diameter of the admission orifice (330) and the diameter of the inlet orifice (110), the length (L) and the diameter (Dc) of the chamber (10) being of such a size so as to define a volume tuned as a function of said determined sound frequencies.

15 Claims, 7 Drawing Sheets

(56) References Cited

U.S. PATENT DOCUMENTS

| | | | | |
|---|---|---|---|---|
| 3,685,611 | A * | 8/1972 | Duvvuri | 181/213 |
| 3,692,141 | A * | 9/1972 | Labussiere et al. | 181/213 |
| 3,890,060 | A * | 6/1975 | Lipstein | 415/119 |
| 3,947,148 | A * | 3/1976 | Holt | 415/119 |
| 4,104,002 | A * | 8/1978 | Ehrich | 415/119 |
| 4,180,141 | A * | 12/1979 | Judd | 181/264 |
| 5,709,529 | A * | 1/1998 | Parzych | 415/119 |
| 5,810,911 | A | 9/1998 | Behrendt et al. | |
| 6,212,790 | B1 | 4/2001 | Stetson | |
| 6,905,305 | B2 * | 6/2005 | James | 415/173.4 |
| 2007/0034444 | A1 * | 2/2007 | Yaoita | 181/224 |
| 2009/0188126 | A1 | 7/2009 | Gaillard et al. | |
| 2009/0241542 | A1 * | 10/2009 | Ono et al. | 60/624 |
| 2011/0016737 | A1 * | 1/2011 | Gaillard et al. | 34/97 |

FOREIGN PATENT DOCUMENTS

| | | | | |
|---|---|---|---|---|
| EP | 0 631 738 | A | 1/1995 | |
| JP | 57024424 | A * | 2/1982 | F02C 7/04 |
| JP | 60 135700 | A | 7/1985 | |
| JP | 07155219 | A | 6/1995 | |
| WO | WO 9211783 | A1 | 7/1992 | |
| WO | WO 2009099399 | A1 * | 8/2009 | F01N 1/18 |

OTHER PUBLICATIONS

Allowed Claims in co-pending U.S. Appl. No. 12/048,810.

Office Action received in U.S. Appl. No. 12/048,810 dated Sep. 20, 2011.

* cited by examiner

SILENCER FOR DRYING APPLIANCE AND QUIET HAIRDRYER

The present invention relates to the field of drying appliances and, in particular, of hair dryers. The present invention relates more particularly to a silencer for a drying appliance such as a hair dryer, as well as a silent hair dryer.

BACKGROUND OF THE INVENTION

Dryers, hair dryers in particular, are generally equipped with a fan or a turbine acting as blower. Often, the turbine is the centrifugal type, producing an airflow piped by walls of a casing of the dryer, to a nozzle concentrating the airflow to obtain effective pressure for drying. The drying function is generally improved by the presence of resistance downstream of the fan or turbine, so as to heat the expelled air. The entry of air at the level of the turbine is generally provided by a grille preventing access to the revolving parts of the turbine and protecting the appliance from fouling. This grille often comprises a first part fixed to the air admission bell of the centrifugal turbine and constituted by ribs (or beads) spaced such that they at least prevent penetration by a child's finger and a second part constituted by a filter made of a grille and/or by open-weave foam and whereof the frame is of such a size that it can screen out dust and hair. Often, this filter is made detachable by various solutions such as being inserted into a cover allowing it to be disassembled and reassembled quickly for easy cleaning.

A problem with drying appliances relates to the often high sound level of the motor and of the fan or the turbine. Indeed, the rotations of the motor and of the fan or of the turbine are sources of noise. The noise generated by such appliances is a function of the power of the motor and of the rotation speed of the turbine. This noise is particularly annoying for the user, especially in the case of hair dryers used close to the ears of users.

Solutions for optimising the yield of the centrifugal turbine and attenuating its sound level are known from the prior art. Certain solutions consist in decreasing the air turbulence generated near the blades by radiating the edge of the admission of the air upstream or downstream of the grille and of the dust filter. Certain solutions of the prior art consist of fitting the hair dryer with screens designed to diminish propagation of sound waves radiating perpendicularly to the air admission. Certain screens are made from insulating material and others are in the form of either a casing pierced with lateral air intake inlets, or a cover enclosing the body of the appliance at the level of the turbine such that this air admission occurs annularly between this body and this cover. The drawback to these solutions is that they are unsatisfactory. In fact, to mask the sound effect of the turbulence generated at the leading edge of the blades of the turbine, the flowing section of the air admission must be decreased to the maximum, to the detriment of the airflow yield of the turbine. Attaining the objective of flow is possible only by increasing the speed of the motor, inducing a decrease in the shelf life of the appliance. Also, the sound attenuation gained is then partly lost by the increase in noise generated by the motor. On the other hand, the lateral air intake inlets do not satisfactorily dampen the noise.

Another problem in the field of drying appliances relates to the fact that noise attenuation cannot generally be added to devices already distributed.

SUMMARY OF THE INVENTION

In this context, it is interesting to propose a silent hair dryer and a silencer for a drying appliance, such as a hair dryer in particular, for reducing noise emitted by the appliance.

An aim of present invention is to eliminate certain disadvantages of the prior art by proposing a silent hair dryer generating little noise.

This aim is attained by a silent hair dryer comprising at least one casing comprising an inlet end, an outlet end and at least one motor driving in rotation at least one turbine sucking in air via at least one admission orifice upstream of the turbine and expelling it via at least one outlet orifice downstream, and generating determiner sound frequencies, said hair dryer comprising a silencer comprising at least one chamber mounted substantially tightly upstream of the admission orifice and comprising an inlet orifice for aspiration of air upstream of the chamber, characterised in that the length and the diameter of the chamber are sized as a function of said determined sound frequencies, the diameter of the chamber being greater than the diameter of the admission orifice and than the diameter of the inlet orifice, by a value determined as a function of said determined sound frequencies.

According to another particular feature, the silencer is made all in one piece with the casing, at the level of the inlet end.

According to another particular feature, the silencer is fixed detachably on the casing, at the level of the inlet end.

According to another particular feature, it comprises a cover fixed detachably on the casing, at the level of the inlet end, by detachable fixing arrangements of the cover, the silencer comprising, on one hand, detachable fixing arrangements on the casing identical to the detachable fixing arrangements of the cover, and on the other hand, in the vicinity of the inlet orifice, arrangements for anchoring fixing arrangements of the cover, such that the silencer can be interposed between the casing and the cover.

According to another particular feature, it comprises a silent turbine, comprising an admission orifice of reduced diameter so as to decrease the noise generated by the turbine and comprising blades whereof the peripheral end is curved in the direction of the direction of rotation of the turbine so as to improve the pressure generated by the turbine, at least to compensate the flow loss resulting from the decrease in the admission diameter of the turbine.

According to another particular feature, it comprises an aerodynamic ball placed upstream of the admission of the turbine to minimise air perturbations entering the turbine and reduce the sound level of the hair dryer.

According to another particular feature, the chamber of the silencer comprises at least one filter of annular shape, substantially filling the volume comprised between the diameter of the chamber and the diameter of the admission orifice or the diameter of the inlet orifice, and comprising at least one porous material, the annular volume and the porosity index of the filter being tuned as a function of the said determined sound frequencies.

According to another particular feature, that the chamber comprises several filters of increasing density in the direction of the admission orifice of the turbine, of annular shape, substantially filling the volume comprised between the diameter of the chamber and the diameter of the admission orifice or the diameter of the inlet orifice and comprising at least one porous material, the volume and the porosity indices of the filters being tuned as a function of the said determined sound frequencies.

According to another particular feature, the porous material present in the filter(s) is a material having open alveoli.

According to another particular feature, the chamber is cylindrical, tapered or polygonal in cross-section.

According to another particular feature, it comprises fixing arrangements on the casing of the hair dryer, at the level of the inlet end.

According to another particular feature, it is equipped with a cover upstream of the inlet orifice of the chamber, the cover comprising fixing arrangements on the silencer, in the vicinity of the inlet orifice.

According to another particular feature, the cover is fitted with at least one filter.

BRIEF DESCRIPTION OF THE DRAWINGS

Other particular features and advantages of the present invention will emerge more clearly from the description hereinbelow, given in reference to the attached diagrams, in which.

DETAILED DESCRIPTION

Figure 5B:
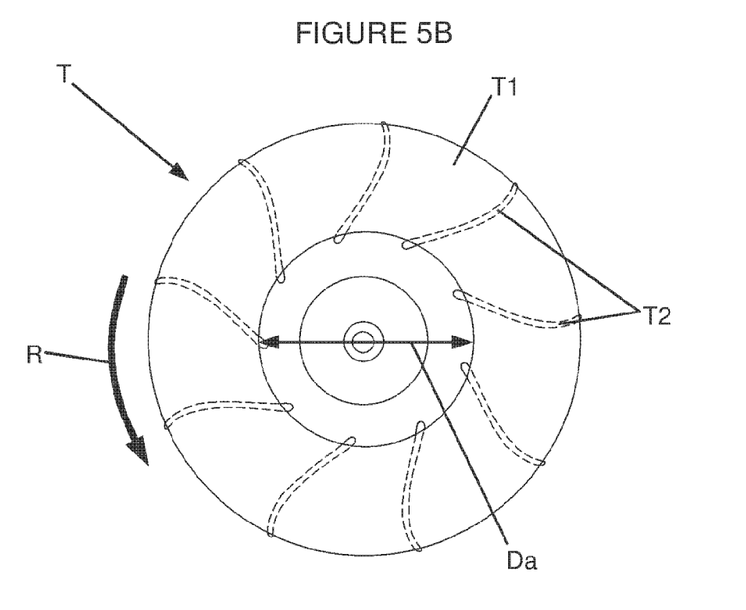
Figure 6A:
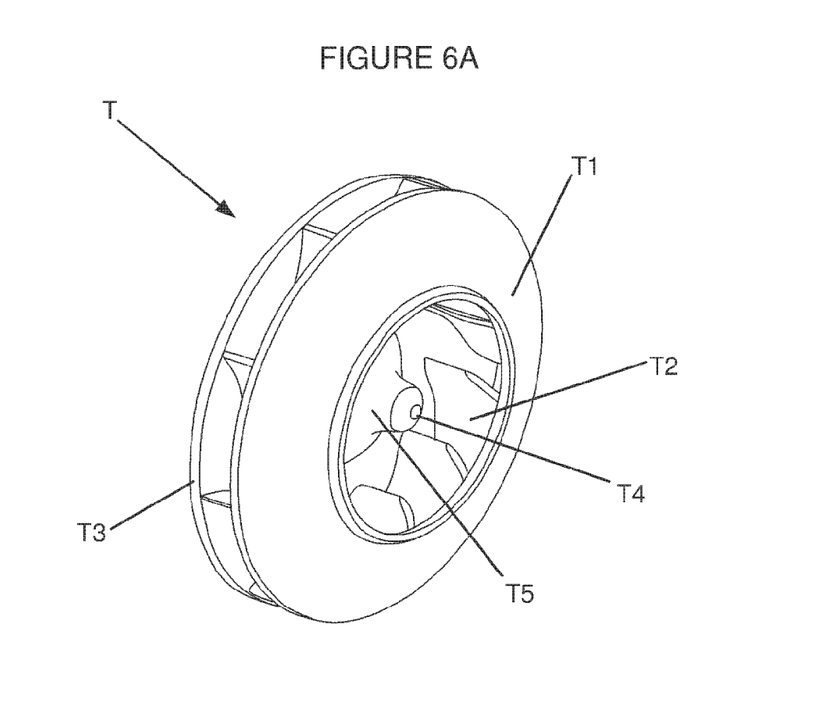
FIGS. 6A and 6B illustrate perspective views of a turbine improved according to certain embodiments of the invention, respectively assembled and in an exploded view.
Figure 6B:
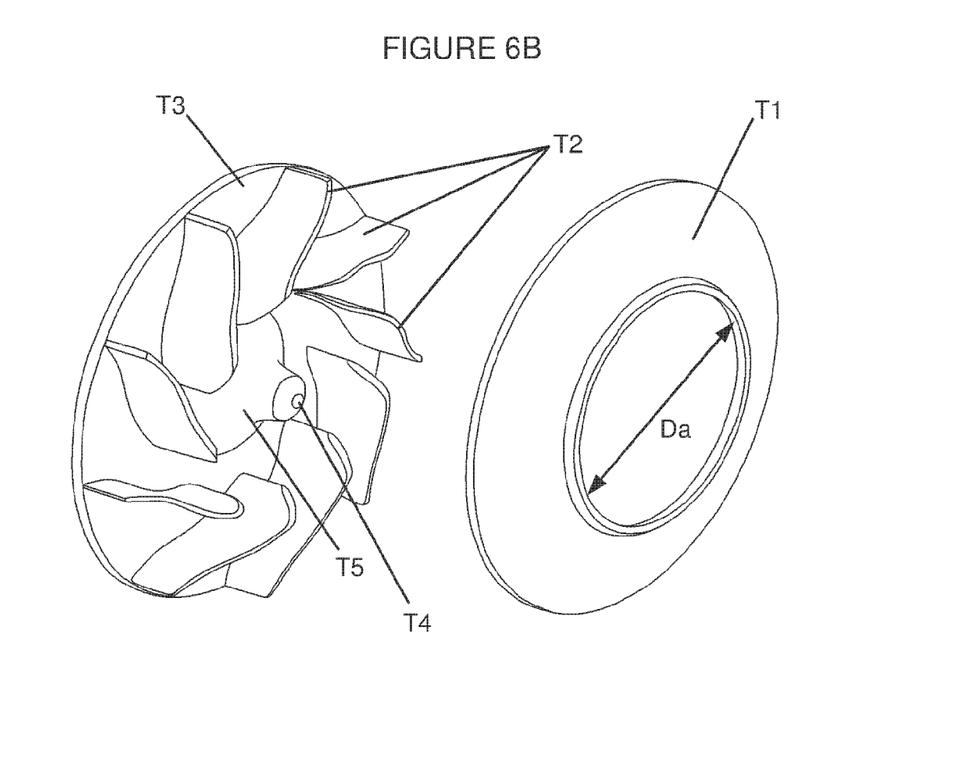
Figure 7:
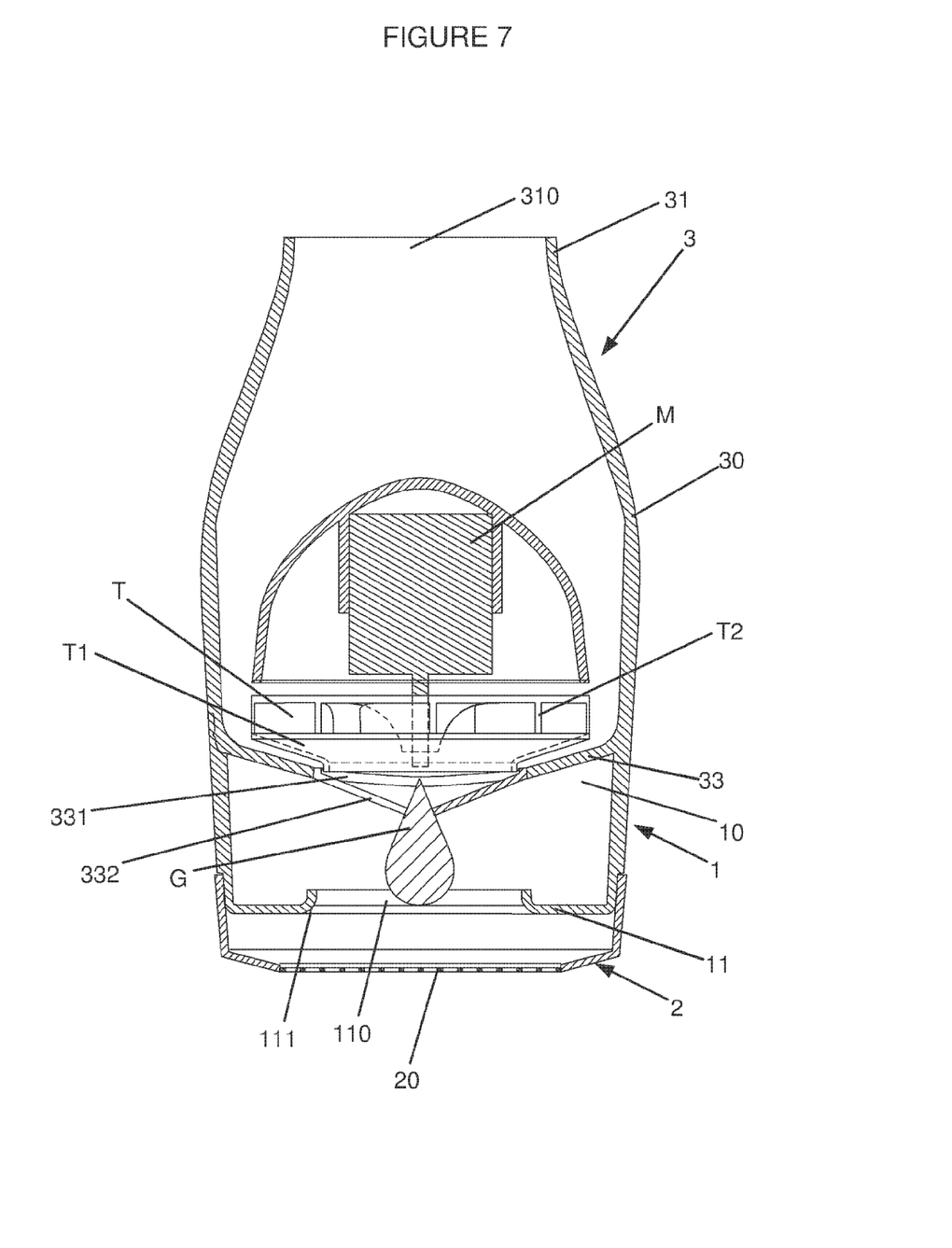
FIG. 7 illustrates a sectional view of a drying appliance fitted with a silencer according to various embodiments of the invention.

The present invention relates to a silencer (1) for drying appliances, in particular for hair dryer (3), and a silent hair dryer. The term drying appliances, or even the term hair dryer, is understood here to mean any type of appliance designed for drying, whether for hair or not. In fact, the invention is adapted to devices and appliances expelling air, heated or not, for example for drying various materials such as, for example, hair. Accordingly, the use which can be made of the invention is not limited to drying of hair. The invention will therefore be limited only to use with an appliance comprising the means or arrangements described herein, or to any adaptation familiar to those skilled in the art. The invention is adapted to any appliance comprising at least one casing (30) having an inlet end (33), an outlet end (31) and at least one motor (M) driving in rotation at least one turbine (T) sucking in air via at least one admission orifice (330) at the level of the inlet end (33) upstream of the turbine (T) and expelling it downstream via at least one outlet orifice (310) at the level of the outlet end (31). This type of appliance drives an airflow (F) through the casing (30), as particularly visible in FIG. 2. This aspirated airflow (F) passes through the inlet (110) and admission (330) orifices, through the silencer (1) which reduces its noise as explained hereinbelow, then passes via the centrifugal turbine which expels it peripherally, between the casing (30) of the appliance and the motor casing (CM). The airflow can of course be heated by a heating device downstream of the turbine, prior to exiting via the outlet orifice (310). As is known from the prior art, the admission orifice (330) can be fitted with a grille (332, FIG. 7) preventing insertion of a child's finger at level of the turbine. This grille can naturally have various shapes and the example of the grille (332) described hereinbelow in FIG. 7 is merely illustrative and in no way limiting. Similarly, as is known from the prior art, the outlet orifice (310) at the level of the discharge end (31) can be fitted with a nozzle concentrating the airflow to boost pressure as it leaves the appliance. In the embodiments shown in the figures, this is a centrifugal turbine creating an airflow (F) generated around the turbine and the motor and piped by the internal walls of the casing (30), though the invention is not limited to this type of arrangement. On the other hand, the turbine (T) illustrated in the figures and particularly visible in FIGS. 5B, 6A and 6B is an example of embodiment of the invention particularly advantageous, but other types of turbines can be utilised, even though the type of turbine described hereinbelow in reference to FIGS. 5B, 6A and 6B is particularly adapted to the principal aim of the invention which is the reduction of noise. Finally, the admission orifice (330) can, according to various embodiments, be arranged in a straight wall at the level of the inlet end (33) or in a tapered wall, as illustrated in the figures. It is evident here that the admission orifice (330) is defined relative to the wall (33) of the inlet end but, in general, the admission relates to the entry of air to the turbine. Therefore, as detailed hereinbelow, when this is a centrifugal turbine (T) comprising a flange (T1) at the level of the air admission in the turbine, as evident particularly in FIGS. 5B, 6A and 6B, the admission orifice important for the aspiration of air and noise generated is in fact the intake orifice of the flange (T1) of the turbine (T), whether the latter is protected or not by a wall (33) of the inlet end. Therefore, in terms here of the admission diameter (Da) of the admission orifice, those of skills in the art will understand that, as a function of the various embodiments detailed hereinbelow, it can be the diameter of the intake orifice of the flange (T1) or the diameter of the admission orifice (330) at the level of the wall (33) in front of the turbine. It is also noted that when the turbine (T) comprises a flange (T1), as illustrated by way of illustration in the figures, and when the turbine is protected by a wall (33) of the inlet end, the flange (T1) and the wall (33) are generally arranged so that the space separating them is sufficiently small to prevent the occurrence of reflux (flowing back) of air exiting from the turbine to the inlet end (33). Also, in these embodiments where the turbine (T) is protected by a wall and comprises a flange (T1), the diameter of the orifice of the wall and the diameter of the entry of the flange are substantially identical, the considerations in diameter being, as explained previously, generally focussed on the entry of air at the level of the turbine (T). Therefore, it can be considered here that the diameter (Da) of the admission orifice (330) corresponds to the inlet diameter of the flange (T1) of the turbine (T) and the two terms are used here in turn to designate the diameter of the air admission in the majority of the embodiments described.

Figure 1:
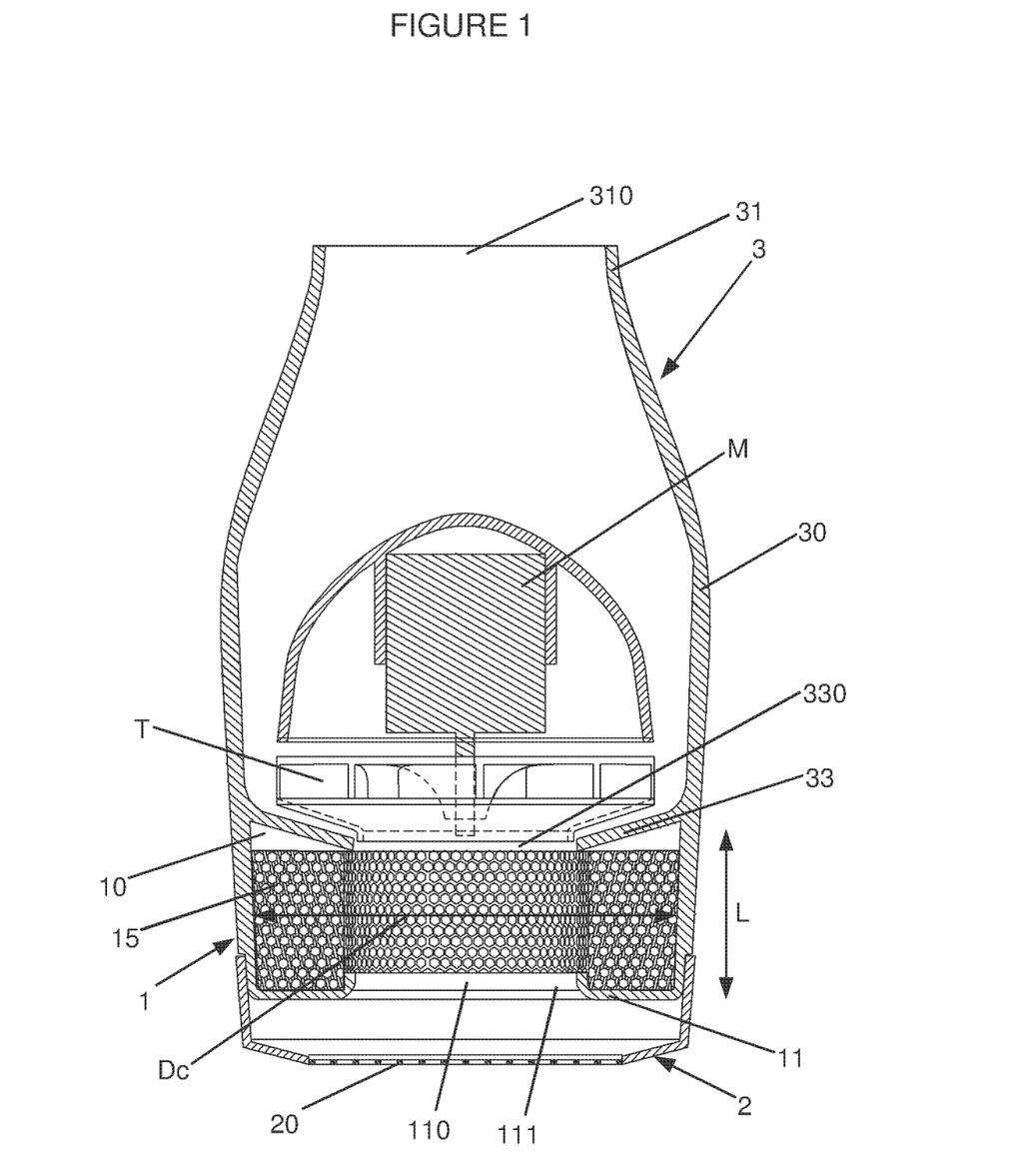
FIG. 1 illustrates a sectional view of a silent drying appliance according to various embodiments of the invention.

The present invention relates to a silencer (1) attenuating noises generated by the motor and the turbine or the fan, as well as a hair dryer (3) comprising at least one silencer (1). The silencer (1) comprises at least one chamber (10) mounted substantially tightly upstream of the admission orifice (330) and comprising an inlet orifice (110) for the aspiration of air upstream of the chamber (10). For instance, this inlet orifice (110) can be arranged in a wall (11) partially closing the silencer. In certain embodiments, this wall (11) comprises a bell (11) whereof the flared edge (111) makes it easy for air to slide to the inside of the chamber (10), thus minimising perturbation. This chamber (10) can, according to various variant embodiments have a cylindrical, tapered or polygonal cross-section or any shape selected by the designers, even though cylindrical or tapered shapes are more aerodynamic and therefore more adapted for use made of them. Similarly, the hair dryer (3), the silencer (1) or all the compartments making it up can naturally have various shapes, even though cylindrical or tapered shapes are preferred. In the present description, the term <<diameter>> of a structure is also understood as the distance (maximum, minimum or average) separating two points situated opposite one another on the structure in question. In general, in the present description, the notion of diameter is utilised to define sizes of airflow sections through an orifice or between two structures. The flow section can of course have any shape circumference since this circumference depends on the structures between which the flow takes place or on the orifice through which the flow takes place. Since the notion of diameter is easily understood in the case of substantially circular structures, the use of this term is understood here in any form which the elements of the invention can assume, such as for example, the hair dryer (3) itself, the chamber (10) or the filter (15) described here. In certain embodiments, the silencer (1) is made all in one piece with the casing (30), at the level of the inlet end (33), as is particularly visible in FIGS. 1 and 3. In other embodiments, the silencer (1) comprises fixing arrangements (35) on the casing (30) of the drying appliance (3), at the level of the inlet end (33), as is particularly visible in FIG. 2. In certain variant embodiments, the silencer is equipped with a cover (2) upstream of the inlet orifice (110) of the chamber (10). As is particularly visible in FIG. 2, the cover (2) comprises fixing arrangements (25) on the silencer (1), in the vicinity of the inlet orifice (110). This cover (2) is fitted with at least one filter (20). As is known per se, this filter can comprise a grille and/or an open-weave (i.e., with open alveoli) material allowing passage of air while filtering particles. In certain variant embodiments, the cover (2) can be made all in one piece with the silencer (1), especially in the case where the silencer (1) is mounted detachably on the casing (30) of the hair dryer (3). In certain particularly advantageous embodiments, the silencer (1) is designed to complement existing hair dryers. In these embodiments, the silencer (1) comprises, on one hand, detachable fixing arrangements (35) on the casing (30) identical to detachable fixing arrangements (25) of the cover (2) on the casing (30) of the drying appliance (3), at the level of the inlet end (33), and on the other hand, in the vicinity of the inlet orifice (110), arrangements for anchoring the fixing arrangements (25) of the cover (2), such that the silencer can be interposed between the casing (30) and the cover (2). Therefore, the silencer (1) can be sold separately to the hair dryer (3), and even be distributed as an add-on to hair dryers (3) already distributed on the market. For instance, there are hair dryers (3) equipped with a removable cover (2) screwed on or fitted on (by a bayonet system) to the inlet end (33) of the hair dryer. The silencer can then include a thread for receiving this cover (2) once unscrewed from the hair dryer (2) and a tapping so that it can be screwed in place of the cover (2). In another example, a more practical use, the silencer can comprise grooves and tenons for cooperating, respectively, with tenons in the hair dryer and the grooves of the cover. Therefore, by simple habitual manipulation (during cleaning for example) the user can improve the hair dryer by adding to it a silencer (1) according to the invention. The invention can therefore provide various forms and dimensions of the silencer (1) for it to be adaptable to various types of hair dryer (3).

Accordingly, the invention also relates to a hair dryer (3) fitted with a silencer according to the invention. In certain embodiments, the silencer (1) is made all in one piece with the casing (30), at the level of the inlet end (33). In other embodiments, the silencer (1) is fixed detachably on the casing (30), at the level of the inlet end (33). In certain embodiments, the silencer is designed to be detachable. In this case, the hair dryer comprises a cover (2) fixed detachably on the casing (30), at the level of the inlet end (33), by detachable fixing arrangements (25) of the cover (2), the silencer (1) comprising, on one hand, detachable fixing arrangements (35) on the casing (30) identical to the detachable fixing arrangements (25) of the cover (2), and on the other hand, in the vicinity of the inlet orifice (110), arrangements for anchoring the fixing arrangements (25) of the cover (2), such that the silencer can be interposed between the casing (30) and the cover (2).

Figure 2:
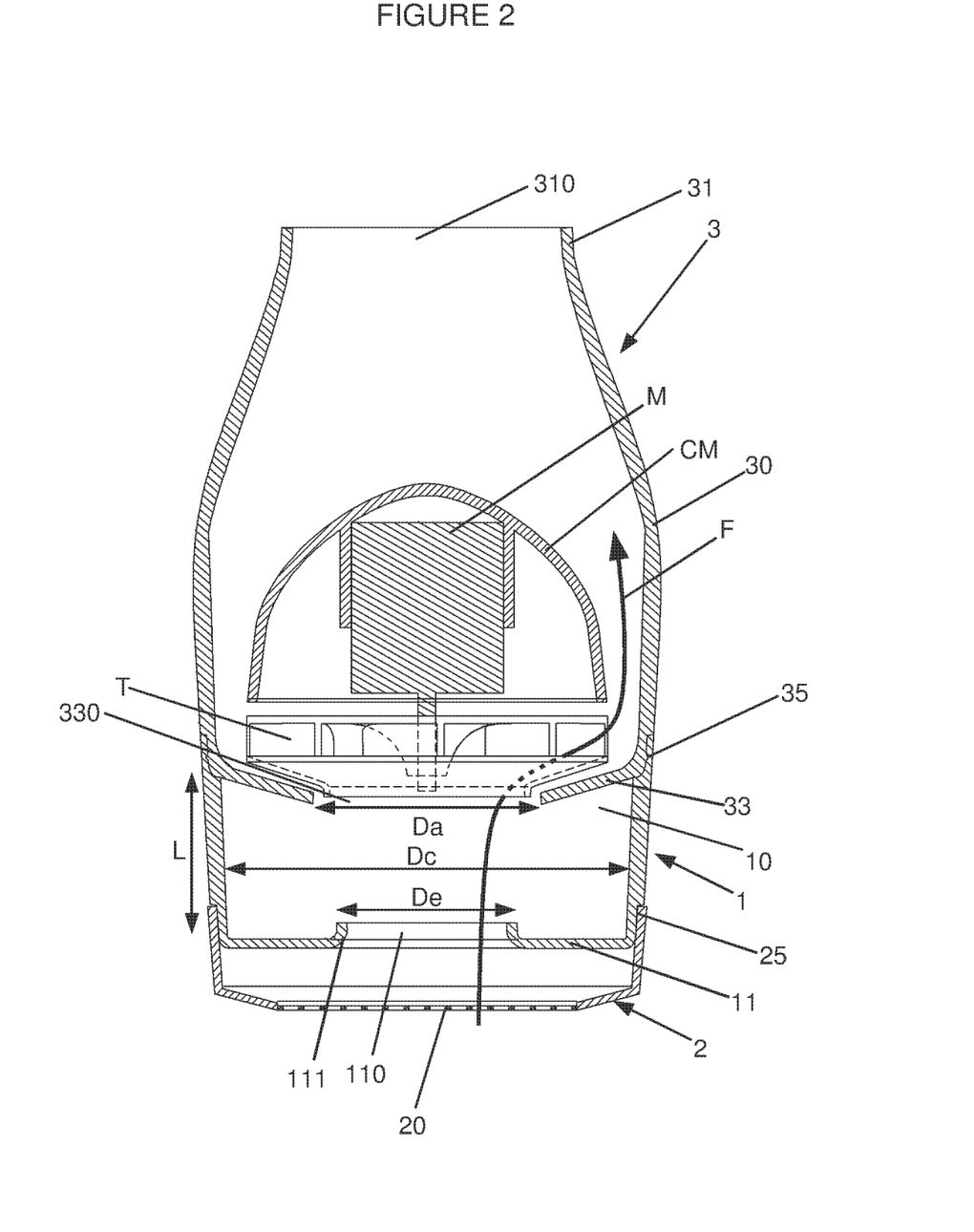
FIG. 2 illustrates a sectional view of a drying appliance fitted with a silencer according to various embodiments of the invention.
Figure 3:
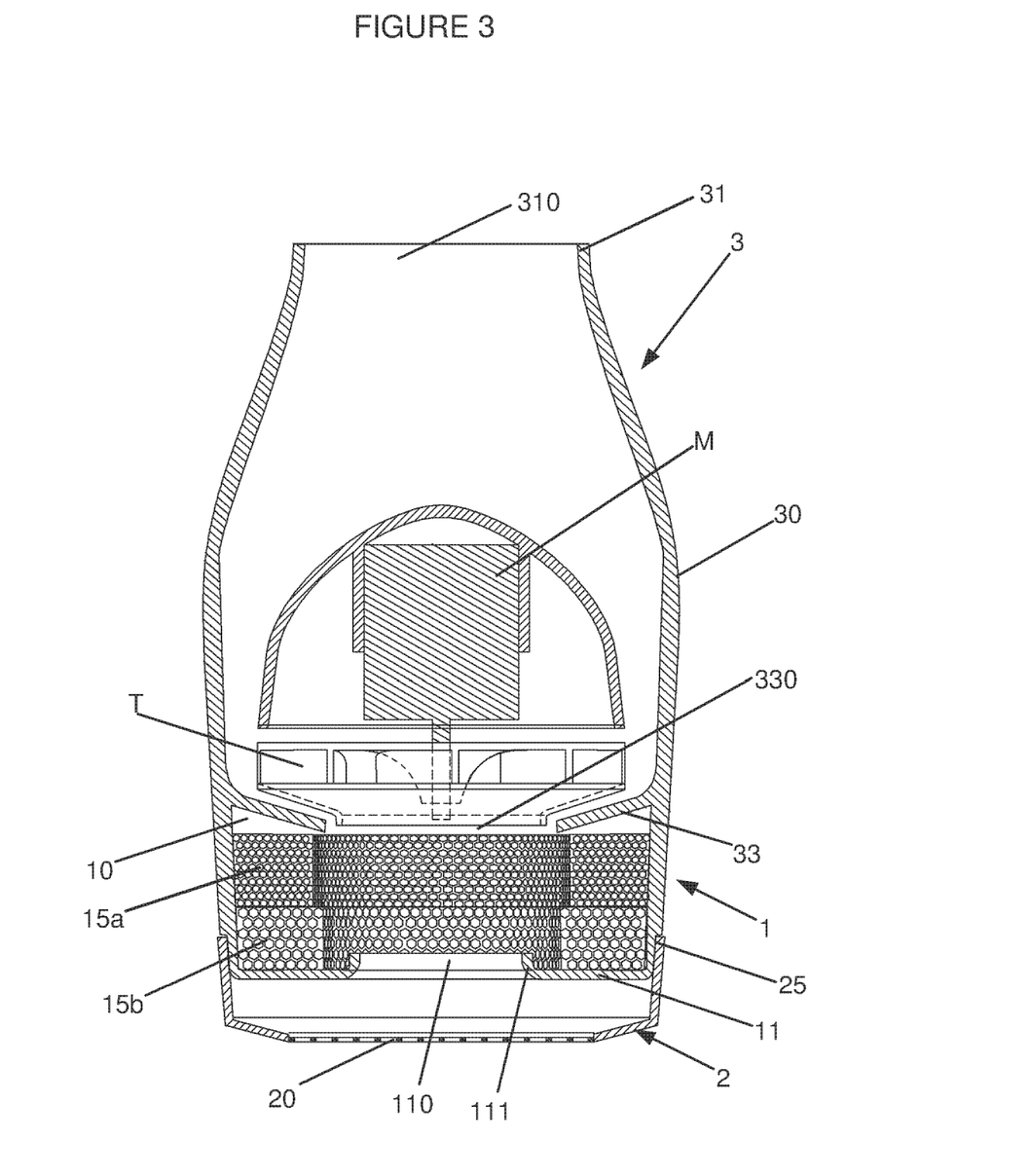
FIG. 3 illustrates a sectional view of a silent drying appliance according to various embodiments of the invention.

More specifically, the chamber (10) of the silencer has a diameter (Dc) greater than the diameter (Da) of the admission orifice (330) (or, equally, of the entry of the flange of the turbine) and of the diameter (De) of the inlet orifice (110). Therefore, the chamber offers an open volume around the airflow for attenuating noise. Also, according to an embodiment of the invention, the diameter (De) of the inlet orifice (110) is less than the diameter (Da) of the admission orifice (330), as is particularly visible in FIGS. 2 and 3, so as to facilitate passage of air and minimise turbulence in the silencer (1) and the hair dryer (3). However, in certain embodiments, these two diameters (Da, De) will be identical, such as for example illustrated in FIG. 1, and in other embodiments the inverse configuration can be considered, even though the configuration illustrated in FIGS. 2 and 3 is more advantageous, since it minimises turbulence and therefore reduces noise. Also, the invention provides an improved turbine detailed hereinbelow in reference to FIGS. 5B, 6A and 6B whereof the inlet diameter (Da) is diminished to minimise noise. These embodiments of the turbines detailed hereinbelow can, in particular and for example, be utilised in embodiments where the admission diameter (Da) in the turbine is substantially identical to the inlet diameter (De) in the silencer. And, the length (L) and the diameter (Dc) of the chamber (10) are sized as a function of the sound frequencies to be attenuated by the silencer (1) or of such size as to define a volume tuned as a function of the sound frequencies to be attenuated by the silencer (1). In fact, the chamber (10) of the silencer (1) according to the invention comprises a volume surrounding (encircling, enclosing) the open passage of airflow through the silencer, thus attenuating noise. The diameter (Dc) of the chamber (10) is greater than the diameter (Da) of the admission orifice (330) and than the diameter (De) of the inlet orifice (110), by a value determined as a function of said determined sound frequencies. The airflow (F) passes through the chamber in its centre, substantially inside a cylinder defined by the smallest diameter of the diameters (Da, De) of the admission orifice (330) and of the inlet orifice (110), though the airflow (F) also reaches the rest of the chamber, in particular an annular volume, defined between the diameter (Dc) of the chamber (10) and at least a diameter of the diameters (Da, De) of the admission orifice (330) and of the inlet orifice (110). The volume of the chamber and in particular this annular volume constitute a sound filter which attenuates the appliance's noise. As a function of the sound frequencies to be attenuated in the appliance on which the silencer is to be installed, the volume of the chamber should have particular dimensions which will be obtained by various combinations of the diameter (Dc) of the chamber and its length (L).

In particular, the hair dryer generates an air flow (F) by rotation of the turbine. This rotation and this flow generate noise which is annoying for the user. It is possible to measure and quantify this noise to determine the sound frequencies which constitute it. A detailed study of the spectrum of sound frequencies emitted by hair dryers when operating determines that the sound frequencies emitted depend mainly on the speed of rotation and the number of blades of the turbine. For example, a centrifugal turbine comprising 9 blades and having a speed of rotation of between 12,000 and 20,000 rpm generates sound frequencies of between 9×12,000/60=1800 Hz and 20,000×9/60=3000 Hz. In general, the spectrum of frequencies emitted by the hair dryer is in fact wider than this range obtained directly by this calculation over the period of rotation of a blade. For example, this type of turbine will in fact generate a very wide spectrum but the measurements presented here have been made only over a spectrum of frequencies of between 250 Hz and 16,000 Hz. Also, when only the most audible frequencies (for example those over 55 audible decibels, dBA) are considered, the spectrum is reduced to frequencies of between 400 Hz and 8000 Hz, the frequencies beyond this range being much less audible (especially those over 6300 Hz).

A measurement taken with a micro located 1 meter from a hair dryer comprising a centrifugal turbine having an inlet ("admission") diameter of the order of 35 mm, an outlet diameter of the order of 64 mm, comprising 9 blades and turning at 13,500 rpm generates pressure of between 500 and 1500 Pa and air flow of between 0.00833 $m^3/s$ and 0.0277 $m^3/s$ (when fitted with the nozzle at its end to concentrate the air flow) and noise whereof the frequency spectrum (for frequencies of acoustic intensity over 55 dBA) is between 400 Hz and 80000 Hz, with the strongest frequencies of acoustic intensity located between 1600 Hz and 2500 Hz.

The invention proposes placing, upstream of the admission, a silencer comprising a chamber of appropriate size, in length and in diameter, to attenuate sound frequencies emitted by the hair dryer. The silencer used during these measurements has an inlet diameter of 0.029 m, that is, less than the admission diameter (0.035 m), to quieten the flow. The flow, now less perturbed, is already generating less noise, though it appears that as a function of the size of the chamber the latter attenuates sound frequencies emitted. The air flow passes to the centre of the chamber, offering a volume around the passage of the flow which attenuates noise. This volume around the passage cross-section of the flow (between the chamber inlet and the turbine admission, defined by their respective diameters) is particularly advantageous by reduction of noise which it allows but also due to the fact that it slightly limits flow (under 10% losses). In fact, this silencer limits flow losses only slightly (of the order of 6% in the case of a classic turbine) and it will become evident later that these flow losses can be reduced further with use of an improved turbine described hereinbelow (losses for example of the order of 3.5% only). However, chambers comprising walls such as baffles or propeller fans produce flow losses which are of the order of 15%. In the example of the hair dryer given hereinabove the dimensions of the chamber enabling efficacious attenuation of frequencies by the silencer are a length of between 0.020 m and 0.060 m (S.I. unit), preferably between 0.030 m and 0.050 m, and a diameter of between 0.040 m and 0.090 m, preferably between 0.050 m and 0.080 m. Various combinations of diameters and length are feasible but it eventuates from measurements taken that for a given length there is a range of optimal diameters and, for a given diameter, there is a range of optimal lengths. It appears therefore that the average values of the volume resulting from these combinations is important for attenuation and that the volume of the chamber must agree with the sound frequencies of the hair dryer by matching its length and its diameter at the same time. For example, during measurements taken with the parameters described hereinabove, it could be determined that for a given length, for example an optimal length of 0.034 m, if the diameter (and therefore the volume) is too small, (for example a diameter of 0.054 m, the average sound frequencies of the hair dryer (of the order of 500 to 8000 Hz, and in particular those between 630 and 6300 Hz which are the most audible by the user), are not well attenuated. For the same length (for example 0.034 m), when the diameter (and therefore the volume) is excessive (for example a diameter of 0.079 m), some ranges of low frequencies (de the order of 500 to 1000 Hz) are not well attenuated, or even amplified. In this example, a compromise is made with a diameter of 0.074 m. Similarly, for a given diameter (for example the diameter of 0.074 m), if the length (and therefore the volume) is too short (for example 0.020 m), the average sound frequencies of the hair dryer are not well attenuated and some frequencies are even amplified, whereas if the length (and therefore the volume) is excessive, some ranges of low frequencies are not well attenuated, or even amplified. In conclusion, it eventuates that the chamber must have an average volume which is correctly matched (of between 0.080 L and 0.220 L, with an optimal value around 0.15 L) and resulting from a compromise between the length (between 0.030 and 0.040 m, preferably 0.034 m) and the diameter (between 0.070 and 0.080 m, preferably 0.074 m). The form and dimensions of the silencer chamber are therefore determining in attenuation.

In this example measurements described hereinabove, the hair dryer without silencer had an acoustic intensity of the order of 68 dBA. Adding a silencer with a matching volume (optimal, with a length of the order of 0.034 m and a diameter of the order of 0.074 m) reduced this acoustic intensity to around 63 dBA. In this example, excessively low chamber volumes, for example with a diameter of 0.054 m and a length of 0.034 m or with a diameter of 0.074 m and a length of 0.020 m, reduced this acoustic intensity to only 64.8 dBA and 65.5 dBA respectively. Similarly, in this example, excessive chamber volumes, for example with a diameter of 0.079 m and a length of 0.034 m or with a diameter of 0.074 m and a length of 0.045 m, reduced this acoustic intensity only to 64.7 dBA and 63.5 dBA, respectively, and amplified some frequencies (respectively around 1000 and 500 Hz). It is evident that the length must be sufficient for the chamber to form a volume to deaden noise, for example a length of over 0.020 m.

The spectrum of sound frequencies emitted by a hair dryer can also depend indirectly on the size of the turbine. In fact, the size of the turbine (characterised mainly by the inlet and outlet diameters of the turbine) mainly influences the characteristics of flow and pressure of the hair dryer. Since the aim in general is to provide a hair dryer whereof the characteristics of flow and pressure are satisfactory (for example a rate of between 0.00833 m3/s and 0.0277 m3/s, preferably between 0.0138 and 0.0194 m3/s, and pressure of between 500 and 1500 Pa, preferably between 700 and 1300 Pa), an increase in the speed of rotation of the turbine will compensate (in terms of flow and pressure) a decrease in the size of the turbine, or an increase in the size of the turbine will compensate (in terms of flow and pressure) a decrease in the speed of rotation. So to retain constant characteristics of flow and pressure, the changes in size of the turbine are compensated by changes in its speed of rotation. As the spectrum of sound frequencies emitted depend on the speed of rotation, it depends indirectly on the size of the turbine if the speed of rotation is modified to retain performance of the hair dryer.

It is thus understood that values of length and optimal diameters given hereinabove by way of example are valid for the hair dryer described, comprising a centrifugal turbine having an "admission" diameter of the order of 0.035 m, an outlet diameter of the order of 0.064 m (and inlet diameter of the silencer at 0.029 m), comprising 9 blades and turning at 13,500 rpm, generating pressure of between 700 and 1400 Pa and air flow of between 0.0138 and 0.0194 m3/s. It is understood therefore also that as a function of the values selected for admission and outlet diameters of the turbine, the speed of rotation of the turbine will optionally be adapted to retain performance of the hair dryer and the dimensions of the chamber of the silencer according to the invention will be adjusted to uncover optimal values (correctly matched as explained hereinabove). Similarly, according to the number of blades, the adjustments will be done as a consequence. But the optimal values given here, that is, a length of between 0.020 and 0.050 m, preferably between 0.030 and 0.040 m, and a diameter of between 0.040 and 0.090 m, preferably between 0.070 and 0.080 m, give a chamber capable of attenuating the majority of sound frequencies emitted by hair dryers in the ranges of frequencies measured here (between 250 and 16000 Hz) and in particular in the most audible range (between 400 and 8000 Hz).

Some embodiments of the invention therefore relate to a hair dryer (3) silencer comprising at least one casing (30) comprising an end inlet (33), an outlet end (31) and at least one motor (M) driving in rotation at least one turbine (T) suck in air via at least one admission orifice (330) upstream of the turbine (T) and expelling it via at least one outlet orifice (31) downstream, generating determined sound frequencies, the hair dryer comprising a silencer (1) comprising at least one chamber (10) mounted in a substantially sealed manner upstream of the admission orifice (330) and comprising an inlet orifice (110) for aspiration of air upstream of the chamber (10), the diameter (Dc) of the chamber (10) being between 0.040 and 0.090 m, and the length (L) being between 0.020 and 0.050 m. In these embodiments, the length (L) and the diameter (Dc) of the chamber (10) could have been dimensioned so as to be matched (or define a matched volume) as a function of said determined sound frequencies of the hair dryer.

Among these embodiments of the invention, some will comprise a silencer with the preferred values (described previously) of diameter (Dc) and length (L) of the chamber: preferably between 0.070 and 0.080 m for the diameter and preferably between 0.030 and 0.040 m for the length (L).

Among these embodiments of the invention, some will comprise a silencer with optimal values (described previously) of diameter (Dc) and length (L) of the chamber: 0.074 m for the diameter and 0.034 m for the length (L).

Also, adding filters made of porous material to the chamber can further improve noise attenuation properties. In the example described hereinabove, with optimum dimensions of the chamber (length of 0.034 m and diameter of 0.074 m), adding a filter of porous material (preferably with open alveolae) further reduces noise by around 1.6 dBA. This therefore results in a hair dryer generating of the order of 61-62 dBA. It is evident that this noise attenuation can be further improved by adjusting the porosity index of the filter as a function of frequencies emitted and dimensions of the chamber. Also, several filters of different indices can be combined to optimise attenuation, as described hereinbelow.

Figure 4:
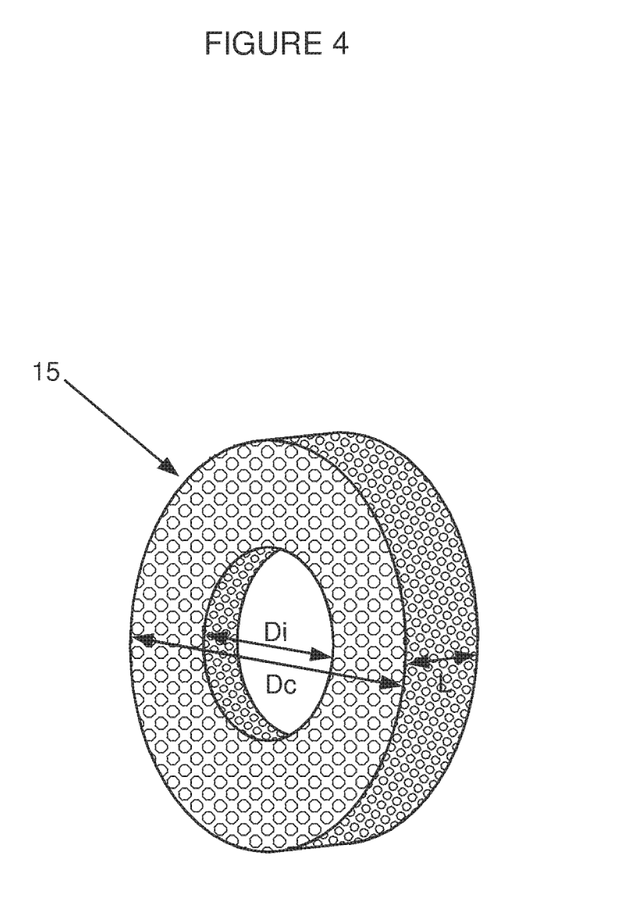
FIG. 4 illustrates a perspective view of a filter made of porous material equipping the devices according to various embodiments of the invention.

In certain particularly advantageous embodiments, the chamber (10) comprises at least one filter (15) of annular shape, as shown in FIG. 4. This annular filter fills the annular volume of the chamber, opened around the passage of the airflow (F) between the inlet and admission orifices and it attenuates noise even better. As illustrated in FIG. 4, this filter has substantially the shape of a ring (the cross-section can vary in shape as a function of the cross-section of the silencer), with an external diameter substantially equal to the diameter of the chamber (Dc) and an internal diameter (Di), for the passage of the airflow (F), substantially equal to at least a diameter of the diameters (Da) of the admission orifice (330) and of the inlet orifice (110). It is noted here that, in certain embodiments, the internal diameter (Di) of the filter(s) (15, 15a, 15b) can be variable over the entire length (L), for example in the case where the diameters of the intake orifice and of the admission orifice are not identical. Therefore, the internal diameter of the filter can fit (follow) the tapered profile described by the diameters of these two orifices. As specified earlier, the exact shape of the cross-sections of the different elements can vary according to diverse variant embodiments and the terms relative to the diameters or to the conicity of the chamber or the internal diameter of the filter (inter alia) are utilise for illustrating variants, but those skilled in the art will appreciate the adaptations which can be made from the forms illustrated here, such as for example square or rectangular cross-sections, in particular with inclined walls for fitting the profile described by the various sizes of the diverse orifices. This filter (15) is preferably made of porous material to allow circulation of the air in the material. Furthermore, the porous material present in the filter(s) (15, 15a, 15b) is preferably an open-weave material (having open or semi-open alveoli or any other intermediate). For instance, the filter can comprise foam of polyurethane or other plastic material, with open alveoli (that is, intercommunicating alveoli so as to facilitate circulation of air through the material: an alveola communicating with its neighbour). The annular volume and the porosity index of the filter (15) are tuned as a function of the sound frequencies to be attenuated by the silencer (1). Therefore, just as when the chamber (10) is empty and attenuates various frequencies as a function of its volume, as in the embodiment illustrated in FIG. 2, the filter (15) attenuates various frequencies as a function of the annular volume which it fills, though the attenuation here is also a function of the porosity index of the filter (15). In certain variant embodiments, the chamber (10) comprises several filters (15a, 15b) of different densities. In particular, in a preferred variant, the density is increasing in the direction of the admission orifice (330) of the turbine (T), as is particularly visible in FIG. 3 showing an embodiment comprising 2 filters. In other variant embodiments, one and the same filter with variable density can be considered. Preferably, this density of the filter will be growing in the direction of the admission orifice (330). Other variant embodiments comprising a single filter of constant density but substantially tapered shape such that part of the filter is more compressed than the rest inside the chamber, resulting from variable density of the filter inside the chamber. Also, according to various variant embodiments, the filters can be separated or not by a wall. These filters (15a, 15b) are also of annular shape and comprise at least one porous material. As previously, the annular volume and the porosity indices of the filters (15) are tuned as a function of the sound frequencies to be attenuated by the silencer (1). In various variants, the filter(s) (15, 15a, 15b) substantially fills (or fill) the annular volume of the chamber (10), as illustrated in FIGS. 2 and 3, but an intermediary configuration can be considered, with an empty annular volume and one or more annular volume(s) comprising at least one filter.

Figure 5A:
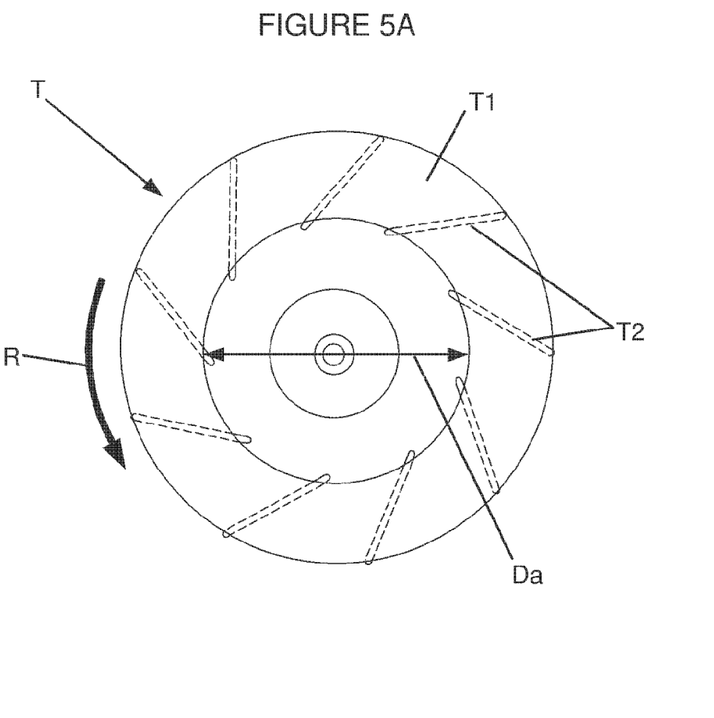
FIGS. 5A and 5B illustrate opposite transparent views, respectively of a turbine known from the prior art and a turbine improved according to certain embodiments of the invention.

FIG. 5A illustrates a centrifugal turbine (T) known from the prior art. This turbine (T) is fitted with a flange (T1) covering the blades (T2) and guiding the aspirated air in between the blades to the circumference of the turbine. The blades (T2) are per se oriented towards the interior of the turbine, in the direction of rotation (R) of the turbine. This orientation of the blades is such that between 2 blades, the flow section at the centre the turbine is less than the flow section at the periphery. The flange (T1) comprises, in its centre, an admission orifice of determined diameter. As mentioned previously, this diameter serves as reference for the air admission and will be defined here as the air admission diameter (Da). Other types of turbines known from the prior art do not comprise a flange, but a wall located upstream plays the same role and limits the entry of air to an admission diameter (Da) of an admission orifice of this wall, as mentioned previously. Therefore, the term admission diameter (Da) will be used here to define this general notion of air admission to the turbine, whether it is fitted with a flange or not (even if it is centrifugal or not). The disadvantage of this type of turbine of the prior art is that it generates noise. There is therefore provision to improve the drying appliance according to the invention by installing therein an improved turbine of the type of that illustrated in FIGS. 5B, 6A and 6B. In this improved turbine (T) according to the invention, the admission diameter (Da) has been reduced (as evident by comparison of FIGS. 5A and 5B), so as to improve the reduction, by the silencer, of the noise generated. It will be noted in the figures that the leading edge of the blades (their central end) protrudes inside the central orifice of the flange. However, this reduction in diameter causes a reduction of the flow (delivery rate) of air. To conserve satisfactory airflow power, in certain embodiments, the peripheral end of the blades (T2) can be curved in the direction of the direction of rotation (R) of the turbine. Therefore, the pressure generated by the turbine (T) is augmented and compensates the loss of airflow resulting from the reduction of the admission diameter. In certain variant embodiments (not illustrated), the central end of the blades (T2) can also be curved, but in the direction inverse to the direction of rotation (R) of the turbine (T). These embodiments of the improved turbine, comprising reduced admission diameter (Da) and curving at least of the peripheral end of the blades (T2) helps improving the attenuation, by the silencer, of the noise generated by the turbine, while conserving satisfactory airflow power. Therefore, since the aim of the present invention is to reduce generated noise, a drying appliance comprising a silencer and such an improved turbine, improving the performances of the appliance and the noise attenuation, is also the subject matter of the present invention. FIG. 6A shows a perspective view of the improved turbine (T) according to the invention. This turbine (T) comprises an axis (T4) by which it is driven in rotation and this axis is fitted with a hub (T5) of substantially tapered form, or substantially having the form of a corolla, a tulip or a bell of curved profile flaring towards the leading edge of the blades, guiding the aspirated airflow towards the blades (T2). The blades (T2) are mounted on a disc (T3) closing the face of the turbine located to the side of the motor. As particularly visible in FIG. 6B, the blades (T2) of the improved turbine of the hair dryer according to certain embodiments of the invention are curved to improve the exit pressure of the turbine. Therefore, the aspirated air is thrust towards the blades (T2) by the internal hub (T5), then guided in the flow section growing between the blades (T2), and pushed by the curved peripheral end of the blades (T2) allowing better pressure.

FIG. 7 illustrates a last refinement of the invention, which will be made to the silencer and/or the hair dryer according to various embodiments of the invention. This refinement consists of adding to the silencer, upstream of the admission orifice, an aerodynamic ball (or bead or drop) (G) reducing perturbation in the area around the inlet of the turbine (T). This ball (G) can, as illustrated in FIG. 7, substantially have the form of a drop of water, that is, comprise a substantially spherical portion and, in the direction of the inlet of the turbine, a substantially conical portion. This ball will be centred relative to the admission orifice (and/or to the intake orifice of the turbine). In certain variant embodiments, the spherical portion will be made of a smooth material, whereas the conical portion will be made of porous material (foam, for example). Other simpler variants in which the two portions are made of identical material can naturally be considered. In the example illustrated in FIG. 7, this ball is fixed by feet (332). For instance, as mentioned previously, the admission orifice can be fitted with a grille (331, FIG. 7) comprising feet or ribs (332) preventing penetration by fingers (children's ideally). These ribs (332) can therefore form fixing of the ball (G) upstream of the admission. This fixing can be conceivable whether there is a grille or not at this level and other types of fixing can of course be adapted, especially by minimising turbulence in the area around the turbine. It will be noted, as is particularly visible in FIG. 7, that the diameter (De) of the intake orifice has been augmented to compensate obstruction of the intake orifice (110) by the ball (G).

Therefore, it is understood that the diverse variant embodiments produce a drying appliance (3) which is very silent due to the presence of the silencer (1), of a silent turbine (T) and a ball (G) upstream of the admission of the turbine, the silencer (1) capable of being fitted with sound-absorbent material. It is easily understood that the invention provides numerous embodiments whereof examples are described here and that these examples are illustrative and can be combined, unless it is evident that they are incompatible. Therefore, the scope of the invention extends to various combinations of the variants described and to the evident adaptations familiar to those of skills in the art.

It must be evident for those skilled in the art that the present invention permits embodiments in numerous other specific forms without departing from the field of application of the invention as claimed. As a consequence, the present embodiments must be considered by way of illustration, but can be modified in the field defined by the scope of the attached claims, and the invention must not be limited to the details given hereinabove.

The invention claimed is:

1. A silent hair dryer comprising:
   at least one casing comprising an inlet end, an outlet end, and at least one motor driving in rotation at least one turbine sucking in air via at least one admission orifice upstream of the turbine and expelling air via at least one outlet orifice downstream, and generating sound frequencies; and
   a silencer comprising at least one chamber mounted substantially tightly upstream of the at least one admission orifice and comprising an inlet orifice for aspiration of air upstream of the at least one chamber,
   wherein a length and a diameter of the chamber are sized as a function of said sound frequencies, the diameter of the chamber being greater than a diameter of the admission orifice and greater than a diameter of the inlet orifice by a value as a function to attenuate said sound frequencies.

2. The silent hair dryer according to claim 1, wherein the silencer is made all in one piece with the casing, at the level of the inlet end.

3. The silent hair dryer according to claim 1, wherein the silencer is fixed detachably on the casing, at the level of the inlet end.

4. The silent hair dryer according to claim 1, further comprising:
   a cover fixed detachably on the casing, at the level of the inlet end, by detachable fixing arrangements of the cover, the silencer comprising detachable fixing arrangements on the casing identical to the detachable fixing arrangements of the cover, and, in a vicinity of the inlet orifice, arrangements for anchoring fixing arrangements of the cover for interposing the silencer between the casing and the cover.

5. The silent hair dryer according to claim 1, further comprising:
a silent turbine comprising an admission orifice of reduced diameter constructed so as to decrease a noise generated by the turbine and comprising blades having a peripheral end curved in a direction of rotation of the turbine to improve a pressure generated by the turbine, and to compensate a flow loss resulting from the decrease in the admission diameter of the turbine.

6. The silent hair dryer according to claim 1, further comprising:
an aerodynamic ball placed upstream of the admission of the turbine to minimise air perturbations entering the turbine and to reduce a sound level of the hair dryer.

7. The silent hair dryer according to claim 1,
wherein the chamber of the silencer comprises at least one filter of annular shape, substantially filling a volume comprised between the diameter of the chamber and the diameter of the admission orifice or the diameter of the inlet orifice, and
wherein the filter comprises at least one porous material, an annular volume and porosity index of the filter being tuned as a function to attenuate said sound frequencies.

8. The silent hair dryer according to claim 1,
wherein the chamber comprises a plurality of filters of increasing density in a direction of the admission orifice of the turbine, each said filter having an annular shape, said plurality of filters substantially filling a volume comprised between the diameter of the chamber and the diameter of the admission orifice or the diameter of the inlet orifice, and
wherein said plurality of filters comprises at least one porous material, a volume and porosity index of the filters being tuned as a function to attenuate said sound frequencies.

9. The silent hair dryer according to claim 7, wherein the porous material present in the filter is a material having open alveoli.

10. The silent hair dryer according to claim 1, wherein the chamber is cylindrical, tapered or polygonal in cross-section.

11. The silent hair dryer according to claim 1, further comprising fixing arrangements on the casing of the hair dryer, at the level of the inlet end.

12. The silent hair dryer according to claim 1, further comprising:
a cover upstream of the inlet orifice of the chamber and including fixing arrangements on the silencer, in a vicinity of the inlet orifice.

13. The silent hair dryer according to claim 12, wherein the cover is fitted with at least one filter.

14. The silent hair dryer according to claim 4, wherein the cover is fitted with at least one filter.

15. The silent hair dryer according to claim 8, wherein the at least one porous material is a material having open alveoli.

* * * * *